(12) United States Patent
Rico-Lattes et al.

(10) Patent No.: US 7,446,230 B2
(45) Date of Patent: Nov. 4, 2008

(54) DIBENZOYLMETHANE-BASED COMPOUNDS, USE AS PHOTOACTIVATABLE SUNSCREENS AND COSMETIC COMPOSITIONS CONTAINING THEM

(75) Inventors: Isabelle Rico-Lattes, Auzielle (FR); Fabienne Wetz, Toulouse (FR); Corinne Routaboul, Ramonville Saint Agne (FR); Alain Denis, Villeurbanne (FR)

(73) Assignees: Laboratoire Bioderma, Lyons (FR); CNRS-Centre National de la Recherche Scientifique, Paris (FR); Universite Paul Sabatier Toulouse 3, Toulouse (FR)

( * ) Notice: Subject to any disclaimer, the term of this patent is extended or adjusted under 35 U.S.C. 154(b) by 251 days.

(21) Appl. No.: 10/564,888

(22) PCT Filed: Jul. 15, 2004

(86) PCT No.: PCT/FR2004/001859

§ 371 (c)(1),
(2), (4) Date: May 18, 2006

(87) PCT Pub. No.: WO2005/009938

PCT Pub. Date: Mar. 2, 2005

(65) Prior Publication Data

US 2007/0025930 A1 Feb. 1, 2007

(30) Foreign Application Priority Data

Jul. 17, 2003 (FR) .................................. 03 08736

(51) Int. Cl.
*C07C 49/00* (2006.01)
*A61K 8/00* (2006.01)
(52) U.S. Cl. .......................... 568/331; 424/59; 424/60
(58) Field of Classification Search ................. 568/331; 424/59, 60
See application file for complete search history.

(56) References Cited

U.S. PATENT DOCUMENTS 6,444,195 B1 9/2002 Cole et al.

FOREIGN PATENT DOCUMENTS

| BR | 0 006 583 A | 7/2002 |
| FR | 2 440 933 | 6/1980 |
| FR | 2 747 038 | 4/1996 |
| FR | 2 750 335 | 7/1996 |
| FR | 2 768 730 | 9/1997 |
| FR | 2 526 658 | 7/2002 |
| JP | 06-095184 | 4/1994 |
| WO | WO 02/49598 A2 | 6/2002 |

OTHER PUBLICATIONS

Marzinzik, Andreas et al., "Solid Support Synthesis of Highly Functionalized Pyrazoles and Isoxazoles; Scaffolds for Molecular Diversity", Tetrahedron Letters, vol. 37, No. 7, pp. 1003-1006, Great Britain, 1996.
Kagawa, Hiroyuki et al.. "3-(4-tert-Butylphenyl)-3-hydroxy-1-(4-methoxyphenyl)-2-propen-1-one: as SHG Active Beta-Diketone", Acta Crystallographica, Section C: Crystal Structure Communications, C49 (12), 2181-3 Coden: Acscee; ISSN: 0108-2701, 1993.
Dubois, M., et al., "Photoisomerisation of the Sunscreen Filter PARSOL 1789", Journal De Chimie Physique et de Physico-Chimie Biologuique, pp. 338-394, L'Oreal, Laboratories, de Recherche Avancee, 1998.
Clark, James et al., "Hydrogen Bonding in Organic Synthesis Part 6 C-Alkylation of Beta-dicarbonyl Compounds Using Tetra-alkylammonium Flourides", Journal of the Chemical Society, Perkin Transactions 1., pp. 1743-1745, 1997.
Gruijl, Frank R., et al., "Wavelength Dependence of Skin Cancer Induction by Ultraviolet Irradiation of Albino Hairless Mice", Cancer Research 53, pp. 53-60, Jan. 1, 1993.
Hauser, Charles R. et al., "The Acylation of Ketones to Form Beta-Diketones or Beta-Keto Aldehydes", Duke University, pp. 59-196, 1949-1950.

*Primary Examiner*—Sikarl A Witherspoon
(74) *Attorney, Agent, or Firm*—Oliff & Berridge, PLC

(57) ABSTRACT

The present invention relates to dibenzoylmethane-based compounds of formula 1,

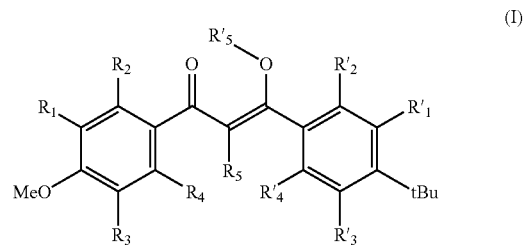

and also to salts or solvates thereof, and to the process for preparing them.

The invention also relates to the use of a compound of formula (I) as an agent for protecting the skin or the hair against UV radiation and to a cosmetic and/or dermatological product, characterized in that it comprises a compound of formula (I) as active principle.

26 Claims, No Drawings

DIBENZOYLMETHANE-BASED COMPOUNDS, USE AS PHOTOACTIVATABLE SUNSCREENS AND COSMETIC COMPOSITIONS CONTAINING THEM

The present invention relates to compounds with good capacity for absorbing ultraviolet radiation, which acquire some of this capacity under light excitation, and whose absorption properties are photostable. The invention also relates to the use of these compounds in cosmetic preparations as UVA screening agents, and to cosmetic and/or dermatological compositions containing such compounds.

The sun emits a combination of light radiation that reaches the surface of the earth: ultraviolet rays, visible rays and infrared rays. In general, a radiation is characterized by its wavelength and its energy, these two magnitudes being inversely proportional. Thus, a short wavelength is associated with high energy. In the context of the present invention, ultraviolet rays are the part of the solar spectrum concerned. This radiation, as a whole, does not exceed 5% of the total energy received on the earth's surface, but its impact on live organisms is very important. The most commonly known of these impacts is sunburn, and the most desired impact is a suntan.

Ultraviolet rays are divided into three major fields: UVA, UVB and UVC.

UVC rays are radiation with a wavelength of between 190 and 290 nm. They are highly energetic and thus have high power to impair biological molecules. They are moreover used as germicides in hospitals. They are in principle stopped by the atmosphere.

UVB rays, with wavelengths of between 290 and 320 nm, represent 2% of the UV rays reaching the surface of the earth. They penetrate partially into the skin, and only 10 to 20% reach the dermis. They are traditionally held responsible for solar erythema, but also induce more important damage especially at the genomic level. They have been attributed with carcinogenic properties in this respect.

UVA rays represent 98% of the UV rays received on the surface of the earth. They are less energetic than UVB rays and have wavelengths ranging from 320 to 400 nm. Above 400 nm is where visible radiation begins. UVA rays penetrate more deeply into the skin than UVB rays. Thus, 20 to 30% reach the middle dermis.

They induce the formation of pigments and are responsible for tanning. In the long term, they have for a long time been attributed with participation in accelerated ageing of the skin, but it is only in about the last ten years that their carcinogenic potential has been recognized. It should also be noted that the first generations of sunscreens did not contain UVA-screening agents, but only UVB-screening agents.

The introduction of a UVA-screening agent became imperative after the publication of scientific articles showing the capacity of UVA rays to induce skin cancers in animals (fish and mice). Specifically, the spectrum of action for the induction of squamous carcinomas (SCC) and basocellular carcinomas (BCC) in hairless mice (de Gruijl F. R., Sterenborg H., Forbes P. D. et al. Cancer Res. 1993; 53: 53-60) shows maximum efficacy for wavelengths in the region of 310 nm in the UVB range and of 360 nm in the UVA range. This second maximum is 10 000 times lower in efficacy than the first. The values presented in the article represent the probability of a photon of given wavelength inducing a lesion of SCC or BCC type. A correction must therefore be made that takes into account the proportion of each of the photons in the solar radiation (UVA rays represent 98% of the radiation, and UVB rays 2%). Thus, after correction, it turns out that UVA rays are only 100 times less efficient than UVB rays in the induction of BCC and SCC cancer in mice. Such a value indeed merited the introduction of a small level of protection against UVA rays.

Thus, in the last about ten years, specific attention has been paid to UVA photoprotection.

Currently, only a small number of molecules are available and permitted in cosmetics for providing anti-UVA protection. One of the compounds most commonly used is, without contest, Parsol 1789 or 4-tert-butyl-4'-methoxydibenzoylmethane [CAS: 70356-09-1]. This molecule has a high coefficient of molar extinction in the UVA range with a maximum absorption efficacy at about 340 nm. However, its photostability is a subject of controversy. Specifically, this molecule suffers degradation under irradiation and leads to benzoic acid derivatives. This degradation also takes place in antisun cosmetic preparations, which leads to a loss of their activity over time, thus during the exposure of the individual. It should be noted that this degradation is dose-dependent. Its negative impact on photoprotection thus depends on the duration of the exposure. It will be greater for a four-hour exposure than for a two-hour exposure. However, for long exposures, unintentional wiping-off, rubbing-off on sand and successive bathing also impair, and probably to a greater extent, the integrity of the protection. Research has thus been undertaken in order to find means for combating the photodegradation of Parsol 1789 and for photostabilizing preparations containing it.

Two approaches may be envisaged:
the first, which has already been widely exploited, consists in adding to the preparation a molecule that can stabilize Parsol 1789 via various as yet unexplained mechanisms (by way of example, mention may be made of various patents: FR 2 768 730 A1, FR 2 747 038 A1, FR 2 750 335 A1, WO 02/49598A2, US 6 444 195 B1, etc.),
the second approach, which has been much less explored, is that of chemical modification of the molecule itself. This modification needs to allow the molecule to conserve its UV-absorbing properties but to limit its propensity to photodegradation.

The present invention thus relates to novel dibenzoylmethane derivatives that have good capacities for absorbing UV radiation, these capacities being photostable and in part photoactivatable, i.e. derivatives whose absorbing power appears in its entirety only when the said dibenzoylmethane derivatives are subjected to UV exposure.

The present invention relates to dibenzoylmethane-based compounds of formula I:

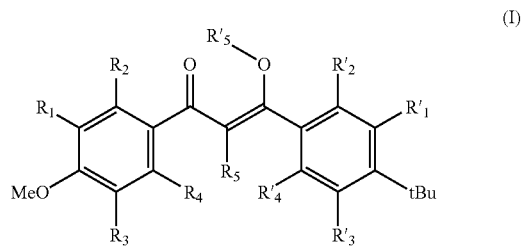

in which, $R_1$, $R'_1$, $R_2$, $R'_2$, $R_3$, $R'_3$, $R_4$ and $R'_4$, which may be identical or different, each represent:
a hydrogen atom,
or a linear or branched alkyl group containing from 1 to 4 carbon atoms, or a linear or branched alkenyl group containing from 1 to 4 carbon atoms, or a linear or branched alkynyl group containing from 1 to 4 carbon atoms, or a C1 to C4 alkoxy group, or a halogen atom, or a hydroxyl group, or an amino group, or a nitro group, or an amido group, or a carbonyl group of formula —CO—Y, in which Y represents a group —OH, —OR or —SR (R representing a C1 to C4 alkyl) or a halogen atom.

$R_5$ and $R'_5$, which are different, each represent:

a hydrogen atom, or a linear or branched alkyl group containing from 1 to 4 carbon atoms, or a linear or branched alkenyl group containing from 1 to 4 carbon atoms, or a linear or branched alkynyl group containing from 1 to 4 carbon atoms, or a linear or branched, saturated or unsaturated acyclic carbon-based chain containing from 5 to 20 carbon atoms, or a linear or branched, saturated or unsaturated acyclic carbon-based chain, functionalized at its end, containing from 5 to 20 carbon atoms, or a linear or branched, saturated or unsaturated acyclic carbon-based chain, comprising a nitrogen atom of amine or amide function and/or an oxygen atom of ether or carboxylic function, containing from 5 to 20 carbon atoms, and also salts or solvates thereof.

The invention more particularly relates to dibenzoylmethane derivatives as defined above, characterized in that $R_1, R'_1, R_2, R'_2, R_3, R'_3, R_4$ and $R'_4$ each represent a hydrogen atom.

The invention also relates to dibenzoylmethane derivatives as defined above, characterized in that $R_5$ and $R'_5$, which are different, each represent:

a hydrogen atom, or a linear or branched alkyl group containing from 1 to 4 carbon atoms, or a linear or branched, saturated or unsaturated acyclic carbon-based chain containing from 5 to 20 carbon atoms.

The invention also relates to dibenzoylmethane derivatives as defined above, characterized in that:

$R_1, R'_1, R_2, R'_2, R_3, R'_3, R_4$ and $R'_4$ each represent a hydrogen atom, and $R_5$ and $R'_5$, which are different, each represent:

a hydrogen atom, or a linear or branched alkyl group containing from 1 to 4 carbon atoms, or a linear or branched, saturated or unsaturated acyclic carbon-based chain containing from 5 to 20 carbon atoms.

The invention also relates to dibenzoylmethane-based compounds of formula I:

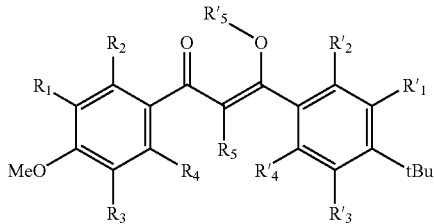

in which, $R_1, R'_1, R_2, R'_2, R_3, R'_3, R_4$ and $R'_4$, which may be identical or different, each represent:

a hydrogen atom, or a linear or branched alkyl group containing from 1 to 4 carbon atoms, or a linear or branched alkenyl group containing from 1 to 4 carbon atoms, or a linear or branched alkynyl group containing from 1 to 4 carbon atoms, or a C1 to C4 alkoxy group, or a halogen atom, or a hydroxyl group, or an amino group, or a nitro group, or an amido group, or a carbonyl group of formula —CO—Y, in which Y represents a group —OH, —OR or —SR (R representing a C1 to C4 alkyl) or a halogen atom.

$R_5$ and $R'_5$, which may be identical or different, each represent:

a linear or branched alkyl group containing from 1 to 4 carbon atoms, or a linear or branched alkenyl group containing from 1 to 4 carbon atoms, or a linear or branched alkynyl group containing from 1 to 4 carbon atoms, or a linear or branched, saturated or unsaturated acyclic carbon-based chain containing from 5 to 20 carbon atoms, or a linear or branched, saturated or unsaturated acyclic carbon-based chain, functionalized at its end, containing from 5 to 20 carbon atoms, or a linear or branched, saturated or unsaturated acyclic carbon-based chain, comprising a nitrogen atom of amine or amide function and/or an oxygen atom of ether or carboxylic function, containing from 5 to 20 carbon atoms, and also salts or solvates thereof.

The invention more particularly relates to dibenzoylmethane derivatives as defined above, characterized in that $R_1, R'_1, R_2, R'_2, R_3, R'_3, R_4$ and $R'_4$ each represent a hydrogen atom.

The invention also relates to dibenzoylmethane derivatives as defined above, characterized in that $R_5$ and $R'_5$, which may be identical or different, each represent:

a linear or branched alkyl group containing from 1 to 4 carbon atoms, or a linear or branched, saturated or unsaturated acyclic carbon-based chain containing from 5 to 20 carbon atoms.

The invention also relates to dibenzoylmethane derivatives as defined above, characterized in that:

$R_1$, $R'_1$, $R_2$, $R'_2$, $R_3$, $R'_3$, $R_4$ and $R'_4$ each represent a hydrogen atom, and $R_5$ and $R'_5$, which may be identical or different, each represent:
- a linear or branched alkyl group containing from 1 to 4 carbon atoms,
- or a linear or branched, saturated or unsaturated acyclic carbon-based chain containing from 5 to 20 carbon atoms.

In general, these dibenzoylmethane derivatives may be obtained from an optionally substituted dibenzoylmethane, via an alkylation reaction according to a protocol similar to those described by Marzinzik and Felder (*Tetrahedron Letters*, Vol. 37, No. 7, pp. 1003-1006, 1996) and Clark and Miller (J. C. S. Perkin I, pp. 1743-1745, 1977).

It involves performing two successive steps: first, the preparation of a dibenzoylmethane/alkylammonium halide, for instance tetrabutylammonium halide, complex, followed by the actual alkylation.

The alkylammonium halide used is an alkylammonium fluoride, chloride, bromide or iodide, preferably tetrabutylammonium fluoride. This tetrabutylammonium halide is either in aqueous solution or in solution in tetrahydrofuran (THF). As a result, the preparation of the dibenzoyl-methane/tetrabutylammonium halide complex is performed either in aqueous medium or in organic medium, preferably in THF.

The actual alkylation is performed in an organic solvent such as tetrahydrofuran (THF), acetonitrile or chloroform, preferably THF. The reaction medium is stirred at room temperature or at reflux, preferably at reflux for 2 to 24 hours and preferably for 8 hours.

The alkylating agent may be an alkyl halide, for instance a fluoroalkane, a chloroalkane, a bromoalkane or an iodoalkane, preferably a bromoalkane, containing from 1 to 20, and preferably 10, carbon atoms.

The optionally substituted starting dibenzoylmethane derivatives, i.e. the compounds of formula (I) in which R5 and R'5 each represent a hydrogen, may be prepared via known synthetic processes, for instance Claisen condensation (see *Organic Reactions*, volume VIII, John Wiley and Sons, 1954), i.e. condensation between a compound of general formula AR—X and AR'—Y, in which AR and AR', which may be identical or different, each represent an optionally monosubstituted or polysubstituted phenyl group and X and Y, which are different, each represent a methoxycarbonyl group or an acetyl group. This condensation reaction is advantageously performed in the presence of a strong base, in the presence of an inert solvent.

The invention also relates to the process for preparing a compound of formula (I) as defined above, characterized in that it includes:

a step of forming a complex in aqueous or organic medium, between a) a molecule of general formula (I) in which $R_1$, $R'_1$, $R_2$, $R'_2$, $R_3$, $R'_3$, $R_4$ and $R'_4$ each represent a group defined in any one of claims 1 to 4 and $R_5$ and $R'_5$, which are identical, each represent a hydrogen atom, and b) an alkylammonium halide, and then a step of substitution of at least one of the hydrogens represented by $R_5$ or $R'_5$, in organic medium via the action of at least one halide of general formula $R_5X$ or $R'_5X$, in which $R_5$ and $R'_5$, which may be identical or different, each represent a group defined above.

The invention more particularly relates to the process as defined above, characterized in that the step of substitution of at least one of the hydrogens represented by $R_5$ or $R'_5$ is an alkylation via the action of at least one alkylating agent of general formula $R_5X$ or $R'_5X$, in which $R_5$ and $R'_5$, which may be identical or different, each represent a linear or branched, saturated or unsaturated acyclic carbon-based chain containing from 1 to 20 carbon atoms.

The dibenzoylmethane derivatives thus obtained have a conjugated system similar to the reference compound described above, i.e. Parsol 1789 or 4-tert-butyl-4'-methoxy-dibenzoylmethane, and thus have ultraviolet-absorbing capacities.

As an illustration of these ultraviolet-absorbing capacities, measurements were taken for two dibenzoylmethane derivatives according to the invention:

for a compound of formula (I) in which $R_1$, $R'_1$, $R_2$, $R'_2$, $R_3$, $R'_3$, $R_4$, $R'_4$ and $R'_5$ each represent a hydrogen atom and $R_5$ represents a saturated linear acyclic carbon-based chain containing 10 carbon atoms, the absorption maximum is (in solution in acetonitrile) at 263 nm with a molar extinction coefficient of 20 000 $l.cm^{-1}.mol^{-1}$. This compound will be referred to hereinbelow as compound C10;

for a compound of formula (I) in which $R_1$, $R'_1$, $R_2$, $R'_2$, $R_3$, $R'_3$, $R_4$, $R'_4$ and $R_5$ each represent a hydrogen atom and $R'_5$ represents a saturated linear acyclic carbon-based chain containing 10 carbon atoms, the absorption maximum is (in solution in acetonitrile) is at 302 nm with a molar extinction coefficient of 17 000 $l.cm^{-1}.mol^{-1}$.

This compound will be referred to hereinbelow as compound O10.

Compound O10 shows strong solvatochromy, which brings the absorption maximum in the UVA range to about 360 nm for organized solvents (for example micellar solutions of sodium dodecyl sulfate). This is likewise the case for compound C10. Furthermore, in organized medium, these two compounds, subjected to ultraviolet radiation, undergo a shift of their maximum absorbance wavelength from UVB to UVA, thus causing the same effect as organization of the system. As a result, the maximum shift of the absorption bands towards UVA is obtained by placing these compounds in organized medium under irradiation, as is the case for an antisun cosmetic preparation under the normal conditions of its use. Irradiation of the preparation amplifies the phenomenon induced by the medium in which the compounds are present. There are therefore two screening molecules present, the absorbing power of which appears in its entirety only when they are subjected to ultraviolet exposure, in an organized medium. The protection capacity of a preparation containing them should thus increase during exposure, rather than decrease, which is the case for preparations containing Parsol 1789 as sole UV-screening agent. This increase in the absorbance at the start of exposure makes it possible to maintain a maximum level of protection for longer. Furthermore, when the absorbance maximum is reached, compounds C10 and O10 are much more photostable than Parsol 1789 with respect to solar irradiation: the absorbance of the preparations suffers a much slower decrease than that observed for preparations comprising Parsol 1789.

The dibenzoylmethane derivatives according to the invention may thus advantageously be used in cosmetic and/or dermatological preparations as sunscreens.

The present invention thus also relates to a cosmetic and/or dermatological composition characterized in that it comprises as active principle at least one compound of formula (I) according to claims 1 to 4, or a salt or solvate thereof, as defined above.

The invention also relates to a composition as defined above, characterized in that it also comprises another active principle.

The invention more particularly relates to a composition as defined above, characterized in that the other active principle is a screening agent chosen from the group consisting of Parsol 1789, 2,4,6-tris[p-(2'-ethylhexyl-1'-oxycarbonyl)anilino]-1,3,5-triazine, 4-(t-butyl)-4'-methoxydibenzoylmethane, 2-hydroxy-4-methoxybenzophenone and 3-(4'-methylbenzylidene)camphor.

The invention more particularly relates to a composition according to the invention, characterized in that it contains from 0.5% to 30% and preferably from 1% to 10% by weight of the said active principle, relative to the total weight of the composition.

The compositions according to the invention may also contain standard cosmetic adjuvants chosen especially from fatty substances, organic solvents, ionic or nonionic thickeners, softeners, antioxidants, opacifiers, stabilizers, emollients, silicones, antifoams, moisturizers, vitamins, fragrances, preserving agents, surfactants, fillers, mineral or organic pigments, sequestrants, polymers, propellants, acidifying or basifying agents, dyes or any other ingredient usually used in cosmetics, in particular for the manufacture of antisun compositions in the form of emulsions.

It may also contain one or more additional hydrophilic or lipophilic UVA-active and/or UVB-active sunscreens.

The present invention also relates to the use of a compound of formula (I) according to the invention, or a salt or solvate thereof, as an agent for protecting the skin or the hair against UV radiation.

The invention also relates to the use of a compound of formula (I) according to the invention, or a salt or solvate thereof, for the preparation of a cosmetic and/or dermatological composition for protecting the skin or the hair against UV radiation.

The invention more particularly relates to the use of a compound of formula (I) according to the invention, or a salt or solvate thereof, as a photoactivatable sunscreen.

The invention also relates to the use of a compound of formula (I) according to the invention, or a salt or solvate thereof, for the preparation of a cosmetic and/or dermatological composition for protecting the skin or the hair against UV radiation, the action of which is photoactivatable and/or prolonged.

The invention also relates to a cosmetic and/or dermatological product, characterized in that it comprises as active principle a compound of formula (I) according to the invention, or a salt or solvate thereof.

The examples that follow illustrate the various aspects of this invention:

EXAMPLES

Preparation of dibenzoylmethane derivatives according to formula (I) in which $R_1$, $R'_1$, $R_2$, $R'_2$, $R_3$, $R'_3$, $R_4$ and $R'_4$ each represent a hydrogen atom and $R_5$ and $R'_5$, which are different, each represent:

a hydrogen atom, or a saturated, linear acyclic carbon-based chain containing 10 carbon atoms.

Production of 3-(4-tert-butylphenyl)-3-decanoxy-1-(4-methoxy-phenyl) prop-2-ene-1-one (compound O10) and 3-(4-tert-butylphenyl)-2-decanyl-1-(4-methoxyphenyl) propane-1,3-dione (compound C10).

Example 1

1-(4-Methoxyphenyl)-3-(4-tert-butylphenyl)propane-1,3-dione (Parsol 1789) [CAS: 70356-09-1] ($1.60 \times 10^{-3}$ mol; 0.50 g) is dissolved in tetrabutylammonium fluoride (TBAF) as a 1M solution in tetrahydrofuran (THF) ($3.20 \times 10^{-3}$ mol; 3 ml; 2 eq.). The mixture is stirred magnetically for 3 hours at room temperature. The alkylating agent, 1-bromodecane ($C_{10}H_{21}Br$) ($3.20 \times 10^{-3}$ mol; 0.71 g; 0.7 ml; 2 eq.), which is itself dissolved in 2 ml of anhydrous THF, is then added to the mixture. The reaction medium is maintained at room temperature with magnetic stirring for 26 hours. A viscous orange residue is obtained after filtration and evaporation of the solvent.

A succession of open columns is then prepared in order to remove the excess reagents (alkylating agent, $C_{10}H_{21}Br$, and TBAF) and to separate the three molecules present in the medium: the unreacted starting molecule, the molecule having for $R_5$ the saturated linear acyclic carbon-based chain containing 10 carbon atoms and an H for $R_1$, $R'_1$, $R_2$, $R'_2$, $R_3$, $R'_3$, R4, $R'_4$ and $R'_5$, and the molecule having for $R'_5$ the saturated linear acyclic carbon-based chain containing 10 carbon atoms and an H for $R_1$, $R'_1$, $R_2$, $R'_2$, $R_3$, $R'_3$, $R_4$, $R'_4$ and $R_5$.

The open columns are prepared with about 40 g of silica 60 gel (0.063-0.200 mm) for 1.0 to 1.5 g of crude product to be separated, the eluent being dichloromethane.

0.50 g of Parsol 1789 gives 0.15 g of compound C10 and 0.10 g of compound O10, i.e. respective yields of 21% and 14%.

Example 2

1-(4-Methoxyphenyl)-3-(4-tert-butylphenyl)propane-1,3-dione (Parsol 1789) [CAS: 70356-09-1] ($16.11 \times 10^{-3}$ mol; 5.00 g) is dissolved in aqueous 75 w/w % tetrabutylammonium fluoride (TBAF) ($24.60 \times 10^{-3}$ mol; 9 ml; 1.5 eq.). The mixture is then evaporated on a rotary evaporator at 80° C. for 3 hours, to give a viscous bright yellow mixture. The medium is then dissolved in 40 ml of anhydrous THF to which is added the alkylating agent 1-bromodecane ($C_{10}H_{21}Br$) ($33.0 \times 10^{-3}$ mol; 7.46 g; 7 ml; 2 eq.). The reaction medium is refluxed with magnetic stirring for 8 hours. A viscous orange residue is obtained after filtration and evaporation of the solvent.

A succession of open columns is then prepared in order to remove the excess reagents (alkylating agent $C_{10}H_{21}Br$ and TBAF) and to separate the three molecules present in the medium: the unreacted starting molecule, the molecule having for $R_5$ the saturated linear acyclic carbon-based chain containing 10 carbon atoms and an H for $R_1$, $R'_1$, $R_2$, $R'_2$, $R_3$, $R'_3$, $R_4$, $R'_4$ and $R'_5$, and the molecule having for $R'_5$ the saturated linear acyclic carbon-based chain containing 10 carbon atoms and an H for $R_1$, $R'_1$, $R_2$, $R'_2$, $R_3$, $R'_3$, $R_4$, $R'_4$ and $R_5$.

The open columns are prepared in the same manner as before.

Separation by HPLC; C18 column; eluent: 5% water/95% acetonitrile; flow rate: 6 ml/minute.

5.00 g of Parsol 1789 give 2.59 g of compound C10 and 2.47 g of compound O10, i.e. respective yields of 34% and 36%.

Characterization of the Products Obtained:

The NMR spectra were acquired using a Bruker ARX 400 MHz machine. The UV absorption spectra were acquired on an HP 8452 A Diode Array Spectrometer. The infrared spectra were acquired on a Perkin-Elmer 1760 X machine.

Compound C10:

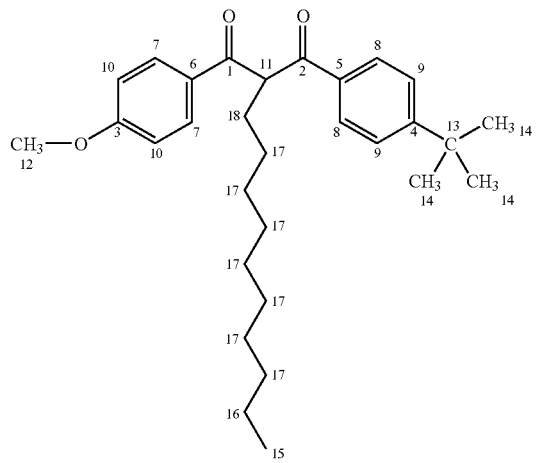

TLC: Rf (CH$_2$Cl$_2$)=0.40.

$^1$H NMR (400 MHz, CDCl$_3$), δppm, J$_{HZ}$: 8.00 (d+d, 2H, J=8.8 and 8.8; H$_7$); 7.93 (d+d, 2H, J=8.4 and 8.4; H$_8$); 7.46 (d+d, 2H, J=8.4 and 8.4; H$_9$); 6.94 (d+d, 2H, J=8.8 and 8.8; H$_{10}$); 5.11 (t, 1H, J=6.6; H$_{11}$); 3,87 (s, 3H, H$_{12}$); 2.12 (m, 2H, H$_{18}$); 1.34 (s, 9H, H$_{14}$); 1.28 (m, 16H, H$_{16}$ and H$_{17}$); 0.89 (t, 3H, J=6.7; H$_{15}$).

$^{13}$C NMR (100 MHz, CDCl$_3$), δppm: 195.9 (C$_2$); 194.9 (C$_1$); 163.8 (C$_3$); 157.1 (C$_4$); 133.7 (C$_5$); 131.0 (C$_1$); 129.3 (C$_6$); 128.8 (C$_9$); 125.8 (C$_8$) 114.1 (C$_7$); 57.5 (C$_{11}$); 55.5 (C$_{12}$); 35.2 (C$_{13}$); 31.9 (C18); 31.1 (C$_{14}$) 29.7-28.5 (C$_{17}$); 22.7 (C$_{16}$); 14.2 (C$_{15}$).

IR (KBr pellet), ν$_{cm}^{-1}$: 2924; 1692; 1663; 1602-1464; 1262; 1171; 844.

UV/vis: dichloromethane: λmax=266 nm; ε=23 000 I.cm$^{-1}$.mol$^{-1}$. Acetonitrile: λmax=263 nm; ε=20 000 I.cm$^{-1}$.mol$^{-1}$.

MS (FAB, MeOH, positive mode) m/z=451 [MH$^+$];
MS (ES, MeOH, positive mode) m/z=451 [MH$^+$].

Compound O10:

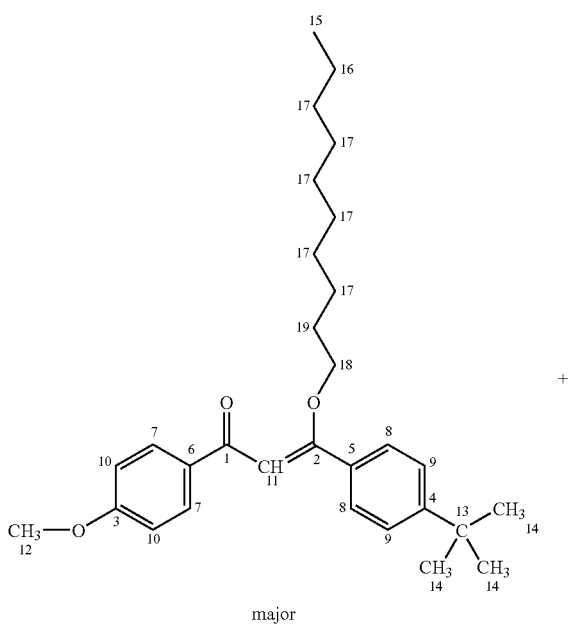

major

+

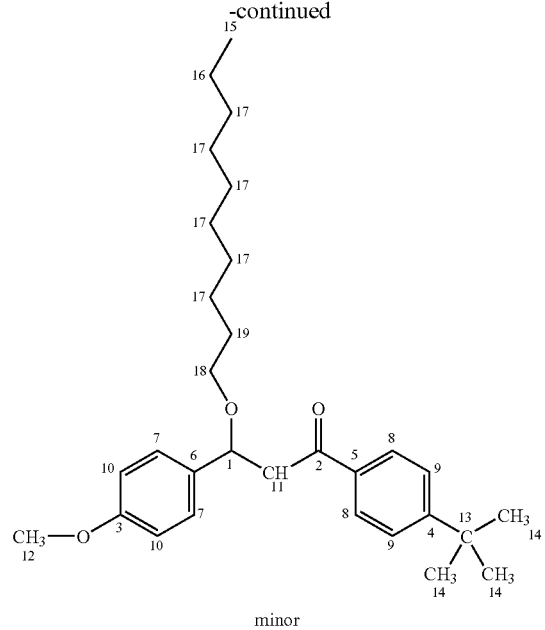

minor

TLC: Rf (CH$_2$Cl$_2$)=0.35.

$^1$H NMR (400 MHz, CDCl$_3$), δppm, J$_{HZ}$: 7.90 (d+d, 2H, J=8.4 and 8.4; H$_7$); 7.42 (d+d, 2H, J=8.2 and 8.2; H$_8$); 7.35 (d+d, 2H, J=8.2 a H$_9$); 6.89 (d+d, 2H, J=8.4 and 8.4; H$_{10}$); 6.46 (s, 1H; H$_{11minor}$); 6.16 (s, H$_{11major}$); 4.13 (t, 2H, J=6.02; H$_{18minor}$); 4.07 (t, 2H, J=6.02; H$_{major}$); 3.86 3H, H$_{12minor}$); 3.84 (s, 3H, H$_{12major}$); 1.86 (m, 2H, H$_{19}$); 1.34 (s, 9H, H$_{14}$); 1.28 (m, 14H, H$_{16}$ and H$_{17}$); 0.90 (t, 3H, J=6.7; H$_{15}$).

$^{13}$C NMR minor (100 MHz, CDCl$_3$), δppm: 188.0 (C$_1$); 169.6 (C$_2$); 163.0 (C$_3$); 155.0 (C$_4$); 133.5 (C$_5$); 133.4 (C$_6$); 130.8 (C$_7$); 129.0 (C$_8$); 124.9 (C$_9$); 113.7 (C$_{10}$); 102.8 (C$_{11}$); 74.5 (C$_{18}$); 55.6 (C$_{12}$); 35.01 (C$_{13}$); 32.1 (C$_{18}$); 31.4 (C$_{14}$); 29.8-26.1 (C$_{17}$ and C$_{19}$); 22.9 (C$_{16}$); 14.3 (C$_{15}$).

$^{13}$C NMR major (100 MHz, CDCl$_3$), δppm: 189.8 (C$_1$); 170.6 (C$_2$); 162.8 (C$_3$); 153.0 (C$_4$); 133.0 (C$_5$); 132.8 (C$_6$); 130.8 (C$_7$); 129.0 (C$_8$); 124.9 (C$_9$); 113.6 (C$_{10}$); 98.7 (C$_{11}$); 69.5 (C$_{18}$); 55.6 (C$_{12}$); 35.01 (C$_{13}$); 32.1 (C$_{18}$); 31.4 (C$_{14}$); 29.8-26.1 (C$_{17}$ and C$_{19}$); 22.9 (C$_{16}$); 14.3 (C$_{15}$).

IR (CaF$_2$ slide), ν$_{-1}$: 2925; 1655; 1603-1464; 1252; 1173.

UV/vis: Acetonitrile: λmax=302 nm; ε=17 000 I.cm$^{-1}$.mol$^{-1}$.

MS (FAB, MeOH, positive mode) m/z=451 [MH$^+$];
MS (ES, MeOH, positive mode) m/z=451 [MH$^+$].

Example 3

Tests of stability towards UV radiation:

By way of example, the changes under irradiation of a base preparation (water-in-oil emulsion) containing the compounds obtained in the above examples, i.e. compound C10 and compound O10, are compared with that of the same preparation containing Parsol 1789 (mass % equivalent for each screening agent).

By way of example, the chosen preparations may be composed as follows:

Glycasil L 0.19%, butyl paraben 0.3%, beeswax 4%, PEG-30 dipolyhydroxystearate 3%, dicapryl carbonate 10%, polyglyceryl-3-diisostearate 1.5%, water 78.64%, xanthan gum 1%, Na$_2$EDTA 0.2%, NaCl 1%; methyl paraben 0.17%

To this common base is added, depending on the case, the compounds C10 or O10 or Parsol 1789 in equivalent mass %. 15 to 20 mg of these preparations are spread onto a quartz slide and the UVA absorbance of the slide is monitored over time under solar irradiation (in the month of June at 43° latitude north between 13.00 h and 16.00 h, mean flux of the solar UV radiation: 4 mW/cm$^2$, Oriel 70380 UV Radiometer—response between 280 nm and 400 nm with a maximum at 370 nm)). The absorbance at 356 nm of the plate with Parsol 1789 decreases by 51% in 1 hour and by 73% in 2 hours. In the same time, the plates that received compound O10 have an absorbance that increases by 16% in 1 hour and 19% in 2 hours. The absorbance of compound C10 increases greatly during the first hour of exposure to sunlight, and then decreases by 27% (relative to the maximum achieved after 1 hour of irradiation) during the second hour. After 2 hours of exposure to sunlight, the absorbance of compound C10 nevertheless remains markedly higher than its initial absorbance (before irradiation). The results obtained are collated in the table below:

| Screening molecules | Variation in the absorbance at 356 nm | |
|---|---|---|
| | Irradiation 1 hour solar UV | Irradiation 2 hours solar UV |
| Parsol 1789 | −51% | −73% |
| compound C10 | +400% | +264% |
| compound O10 | +16% | +19% |

The two test compounds thus show better photostability than Parsol 1789.

However, their molar extinction coefficient is about 30% less than that of Parsol 1789 (when the absorption maximum is achieved by irradiation). It may thus be possible to use the dibenzoylmethane derivatives according to the invention in combination with other screening agents such as Parsol 1789, the dibenzoylmethane derivatives according to the invention protecting Parsol 1789 by means of a screening effect. This combination makes it possible to use a minimum mass of screening agent for a maximum screening effect.

By way of example, a preparation similar to the preceding preparations containing 1% by mass of screening agents in total, of which 32.5% of Parsol 1789, 35% of compound C10 and 32.5% of compound O10 (molar %) was irradiated with sunlight under the same conditions as above and its change was compared with that of a preparation containing 1% by mass of Parsol 1789. The mixed preparation conserves its starting UVA absorbance (or a higher absorbance) for 1 hour, and this absorbance decreases by 33% after 2 hours. The preparation containing only Parsol 1789 undergoes a uniform decrease in absorbance from the start of the exposure. This decrease reaches 51% in 1 hour and 73% in 2 hours.

By way of example, a preparation similar to the previous preparations containing 1% by mass of screening agents, of which 10% of Parsol 1789, 30% of compound C10 and 60% of compound O10 (molar %) was irradiated with sunlight under the same conditions as above, and its change was compared with that of a preparation containing 1% by mass of Parsol 1789. The mixed preparation maintains its starting UVA absorbance (or a higher absorbance) for 2 hours 30 minutes.

The invention claimed is:

1. A compound, selected from the group consisting of a dibenzoylmethane-based compound of formula (I),

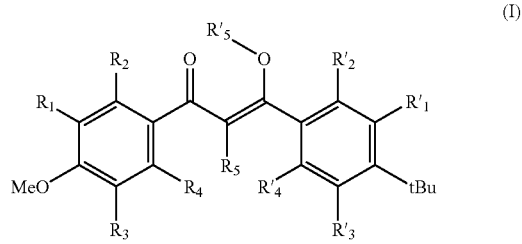

a salt of the dibenzoylmethane-based compound, and a solvate of the dibenzoylmethane-based compound, wherein:

$R_1$, $R'_1$, $R_2$, $R'_2$, $R_3$, $R'_3$, $R_4$ and $R'_4$ each independently represents a member selected from the group consisting of:
a hydrogen atom;
a linear or branched alkyl group containing from 1 to 4 carbon atoms;
a linear or branched alkenyl group containing from 1 to 4 carbon atoms;
a linear or branched alkynyl group containing from 1 to 4 carbon atoms;
a $C_1$ to $C_4$ alkoxy group;
a halogen atom;
a hydroxyl group;
an amino group;
a nitro group;
an amido group; and
a carbonyl group of formula —CO—Y where Y represents a halogen atom, a hydroxyl group, an —OR group or an —SR group, where R represents a $C_1$ to $C_4$ alkyl group;

$R_5$ and $R'_5$ each independently represents a member selected from the group consisting of:
a hydrogen atom;
a linear or branched alkyl group containing from 1 to 4 carbon atoms; and
a linear or branched, saturated or unsaturated acyclic carbon-based chain containing from 5 to 20 carbon atoms; and $R_5$ is different from $R'_5$.

2. The compound of claim 1, wherein $R_1$, $R'_1$, $R_2$, $R'_2$, $R_3$, $R'_3$, $R_4$, and $R'_4$ each represents a hydrogen atom.

3. The compound of claim 1, wherein:
$R_1$, $R'_1$, $R_2$, $R'_2$, $R_3$, $R'_3$, $R_4$, and $R'_4$ each represents a hydrogen atom; and
$R_5$ and $R'_5$ each independently represents a hydrogen atom or a saturated linear acyclic carbon-based chain containing 10 carbon atoms.

4. A photoactivatable sunscreen comprising the compound of claim 1 as an active ingredient.

5. A cosmetic and/or dermatological composition, comprising the photoactivatable sunscreen of claim 4.

6. The cosmetic and/or dermatological composition of claim 5, further comprising a screening agent selected from the group consisting of:4-tert-butyl-4'-methoxy-dibenzoylmethane, 2,4, 6-tris[p-(2'-ethylhexyl-1'-oxycarbonyl)anilino]-1,3,5-triazine, 4-(t-butyl)-4'-methoxydibenzoylmethane, 2-hydroxy-4-methoxybenzophenone and 3-(4'-methylbenzylidene)camphor.

7. The cosmetic and/or dermatological composition of claim 5, wherein the active ingredient is present in an amount of from about 0.5 to about 30% by weight relative to a total weight of the composition.

8. The cosmetic and/or dermatological composition of claim 5, wherein the active ingredient is present in an amount of from about 1 to about 10% by weight relative to a total weight of the composition.

9. A method of protecting skin against sunlight, comprising applying the compound of claim 1 to skin that will be exposed to sunlight.

10. A cosmetic and/or dermatological composition for protecting skin and/or hair against UV radiation, comprising the compound of claim 1 as an active ingredient, wherein the composition is photoactivatable and/or suitable for prolonged use.

11. A method of protecting skin and/or hair against UV radiation, comprising applying the compound of claim 1 to skin and/or hair that will be exposed to UV radiation.

12. A process for preparing the compound of claim 1, comprising:
forming a complex in aqueous or organic medium, between a precursor molecule of general formula (I) where $R_5$ represents a first precursor hydrogen atom and $R'_5$ represents a second precursor hydrogen atom, and an alkylanimonium halide; and
substituting at least one of the precursor hydrogen atoms through the action of at least one of a halide of the formula $R_6X$, and a halide of formula $R_7X$, where $R_6$ and $R_7$ are different and each independently represents a member selected from the group consisting of:
a linear or branched alkyl group containing from 1 to 4 carbon atoms; and
a linear or branched, saturated or unsaturated acyclic carbon-based chain containing from 5 to 20 carbon atoms.

13. The process of claim 12, wherein:
$R_6X$ and $R_7X$ are alkylating agents; and
$R_6X$ and $R_7X$ each independently represents a linear or branched, saturated or unsaturated acyclic carbon-based chain containing from 1 to 20 carbon atoms.

14. 3-(4-tert-Butylphenyl)-3-decanoxyl-1-(4-methoxyphenyl)prop-2-ene-1-one.

15. 3-(4-tert-Butylphenyl)-2-decanyl-1-(4-methoxyphenyl)propane-1,3-dione.

16. A compound, selected from the group consisting of a dibenzoylmethane-based compound of formula (I)

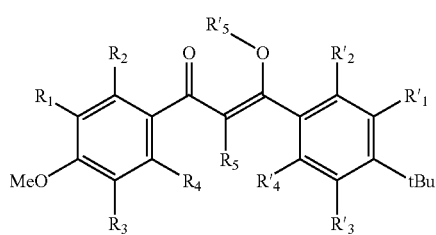

(I)

a salt of the dibenzoylmethane-based compound, and a solvate of the dibenzoylmethane-based compound, wherein:
$R_1$, $R'_1$, $R_2$, $R'_2$, $R_3$, $R'_3$, $R_4$ and $R'_4$ each independently represents a member selected from the group consisting of:
a hydrogen atom;
a linear or branched alkyl group containing from 1 to 4 carbon atoms;
a linear or branched alkenyl group containing from 1 to 4 carbon atoms;
a linear or branched alkynyl group containing from 1 to 4 carbon atoms;
a $C_1$ to $C_4$ alkoxy group;
a halogen atom;
a hydroxyl group;
an amino group;
a nitro group;
an amido group; and
a carbonyl group of formula —CO—Y where Y represents a halogen atom, a hydroxyl group, an —OR group or an —SR group, where R represents a $C_1$ to $C_4$ alkyl group; and
$R_5$ and $R'_5$ each independently represents a member selected from the group consisting of:
a linear or branched alkyl group containing from 1 to 4 carbon atoms;
a linear or branched alkenyl group containing from 1 to 4 carbon atoms;
a linear or branched alkynyl group containing from 1 to 4 carbon atoms;
a linear or branched, saturated or unsaturated acyclic carbon-based chain containing from 5 to 20 carbon atoms;
a linear or branched, saturated or unsaturated acyclic carbon-based chain, functionalized at its end, containing from 5 to 20 carbon atoms; and
a linear or branched, saturated or unsaturated acyclic carbon-based chain, comprising a nitrogen atom of amine or amide function and/or an oxygen atom of ether or carboxylic function, containing from 5 to 20 carbon atoms.

17. A photoactivatable sunscreen comprising the compound of claim 16 as an active ingredient.

18. A cosmetic and/or dermatological composition, comprising the photoactivatable sunscreen of claim 17.

19. The cosmetic and/or dermatological composition of claim 18, further comprising a screening agent selected from the group consisting of:4-tert butyl-4'-methoxy-dibenzoylmethane, 2,4,6-tris[p-(2'-ethylhexyl-1'-oxycarbonyl)anilino]-1,3,5-triazine, 4-(t-butyl)-4'-methoxydibenzoylmethane, 2-hydroxy-4-methoxybenzophenone and 3-(4'-methylbenzylidene)camphor.

20. The cosmetic and/or dermatological composition of claim 18, wherein the active ingredient is present in an amount of from about 0.5 to about 30% by weight relative to a total weight of the composition.

21. The cosmetic and/or dermatological composition of claim 18, wherein the active ingredient is present in an amount of from about ito about 10% by weight relative to a total weight of the composition.

22. A method of protecting skin against sunlight, comprising applying the compound of claim 16 to skin that will be exposed to sunlight.

23. A cosmetic and/or dermatological composition for protecting skin and/or hair against UV radiation, comprising the compound of claim 16 as an active ingredient, wherein the composition is photoactivatable and/or suitable for prolonged use.

24. A method of protecting skin and/or hair against UV radiation, comprising applying the compound of claim 16 to skin and/or hair that will be exposed to UV radiation.

25. A process for preparing the compound of claim 16, comprising:
forming a complex in aqueous or organic medium, between a precursor molecule of general formula (I) where $R_5$ represents a first precursor hydrogen atom and $R'_5$ represents a second precursor hydrogen atom, and an alkylammonium halide; and substituting the precursor hydrogen atoms through the action of a halide of formula $R_6X$ and a halide of formula $R_7X$, where $R_6$ and $R_7$ each independently represents a member selected from the group consisting of:
- a linear or branched alkyl group containing from 1 to 4 carbon atoms;
- a linear or branched alkenyl group containing from 1 to 4 carbon atoms;
- a linear or branched alkynyl group containing from 1 to 4 carbon atoms;
- a linear or branched, saturated or unsaturated acyclic carbon-based chain containing from 5 to 20 carbon atoms;
- a linear or branched, saturated or unsaturated acyclic carbon-based chain, functionalized at its end, containing from 5 to 20 carbon atoms; and
- a linear or branched, saturated or unsaturated acyclic carbon-based chain, comprising a nitrogen atom of amine or amide function and/or an oxygen atom of ether or carboxylic function, containing from 5 to 20 carbon atoms.

26. The process of claim 25, wherein:

$R_6X$ and $R_7X$ are alkylating agents; and $R_6X$ and $R_7X$ each independently represents a linear or branched, saturated or unsaturated acyclic carbon-based chain containing from 1 to 20 carbon atoms.

* * * * *